United States Patent
Sakuta

(10) Patent No.: US 8,828,410 B2
(45) Date of Patent: Sep. 9, 2014

(54) PASTY COMPOSITION AND COSMETICS CONTAINING THE SAME

(75) Inventor: Koji Sakuta, Usuigun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 2025 days.

(21) Appl. No.: 10/488,536

(22) PCT Filed: Sep. 3, 2002

(86) PCT No.: PCT/JP02/08955
§ 371 (c)(1),
(2), (4) Date: Mar. 4, 2004

(87) PCT Pub. No.: WO03/020828
PCT Pub. Date: Mar. 13, 2003

(65) Prior Publication Data
US 2004/0253197 A1 Dec. 16, 2004

(30) Foreign Application Priority Data
Sep. 4, 2001 (JP) ................................. 2001-267608

(51) Int. Cl.
*A61Q 19/00* (2006.01)
*A61Q 17/04* (2006.01)
*A61K 8/894* (2006.01)
*A61Q 15/00* (2006.01)
*C08L 83/12* (2006.01)
*A61Q 5/00* (2006.01)
*A61Q 1/02* (2006.01)
*A61Q 1/06* (2006.01)
*A61Q 1/10* (2006.01)

(52) U.S. Cl.
CPC ................. *A61K 8/894* (2013.01); *A61Q 17/04* (2013.01); *A61Q 1/06* (2013.01); *A61Q 15/00* (2013.01); *C08L 83/12* (2013.01); *A61Q 1/10* (2013.01); *A61Q 19/00* (2013.01); *A61Q 5/00* (2013.01); *A61Q 1/02* (2013.01)
USPC .......................... 424/400; 424/401; 424/70.12

(58) Field of Classification Search
USPC ................................................ 424/70.12, 401
See application file for complete search history.

(56) References Cited

U.S. PATENT DOCUMENTS 5,993,832 A * 11/1999 Lorant et al. ................... 424/401
6,544,532 B1 * 4/2003 Jager-Lezer et al. .......... 424/401
2002/0114771 A1 * 8/2002 Nakanishi ................... 424/70.12

* cited by examiner

*Primary Examiner* — Frederick Krass
*Assistant Examiner* — Tracy Liu
(74) *Attorney, Agent, or Firm* — Millen, White, Zelano & Branigan, P.C.

(57) ABSTRACT

This invention is a cosmetic material containing a pasty composition obtained by adding at least one acidic substance selected from a group comprising organic acids, phosphoric acid and phosphates to a mixture comprising a crosslinking type organopolysiloxane polymer having a polyoxyalkylene group and a liquid oil, adding a basic neutralizing agent to adjust the pH to 5-8, and removing volatile components by heating and/or decompression. This pasty composition is a composition wherein the propionaldehyde amount produced by adding an identical amount of water to the composition and heating at 60° C. for 24 hours is 100 ppm or less.

31 Claims, No Drawings

PASTY COMPOSITION AND COSMETICS CONTAINING THE SAME

FIELD OF THE INVENTION

This invention relates to a pasty composition comprising a crosslinking type organopolysiloxane polymer having a hydrophilic organic group, and a liquid oil, and more particularly relates to a pasty composition which not only does not have an odor, but whereof the pH does not fall and which does not generate an unpleasant odor over time even when blended with an emulsifying system. It further relates to a method of manufacturing this composition, and to a cosmetic material with which this composition is blended.

BACKGROUND OF THE INVENTION

Silicone oil, on account of its safety, has long been used as a base oil in various compositions in many fields, including cosmetics.

In particular, low viscosity silicone oil of not more than 100 mm$^2$/s is attracting attention with a view to extensive use in cosmetic skin care and make-up on account of its outstanding extensibility, fresh feeling and safety.

However, if a pasty composition without fluidity is prepared using low viscosity silicone oil as a base oil, the addition amount of thickener must be increased, so it is difficult to obtain a smooth, uniform composition, and as the low viscosity silicone oil easily separated and was released from the composition so obtained, its stability was low. In order to solve this problem, the use of organic materials as thickeners for low viscosity silicone oil has been proposed, examples being dextrin fatty acid esters (Tokkai Sho 62-121764, 62-143971, 62-143970, 63-159489) sucrose fatty acid esters (Tokkai Sho 63-235366), trimethylsilyl polyvinyl alcohol and trimethylsilyl polysaccharides (Tokkai Sho 62-240335), fatty acid ester group-containing cellulose ether (Tokkai Sho 63-260955), and organically-modified clay minerals (Tokkai Sho 62-45656, 62-54759, 63-72779).

However, when these organic or inorganic materials are used as thickeners, there is a problem that the inherent fresh feeling and high extensibility of the low viscosity silicone oil, decline.

A method of obtaining a uniform pasty composition was therefore proposed using a specific organopolysiloxane polymer as a thickener, and treating it with a low viscosity silicone oil under a shear force (Tokkai Hei 02-43263).

In the field of cosmetics, not only oil but water is often blended as a required component of the composition. In such a case, although a surfactant is used according to conventional methods, it is difficult to distribute the silicone oil and water uniformly and stably, and although the silicone thickener disclosed in Tokkai Hei 02-43263 has excellent thickening qualities with regard to silicone oil, it has the disadvantage that when water is blended, it does not disperse uniformly. In addition, some surfactants irritate the skin, which is undesirable.

In order to solve this problem, Tokkai Hei 04-272932 and 05-140320 propose introducing a polyoxyalkylene group into the molecule of the silicone thickener. Although the composition disclosed therein has excellent emulsifying characteristics, it has the disadvantage that if the composition is stored over a long period of time, the pH falls, and the emulsion emits an unpleasant odor.

A polyether-modified organopolysiloxane can be purified by treating it with an acidic solution (Tokko Hei 07-91389) or by treating unsaturated groups by hydrogenation (Tokkai Hei 07-330907). If these purification methods are applied to this crosslinking type polymer, when treating with corrosive aqueous acids such as hydrochloric acid solution, if the apparatus used does not have a glass lining, the apparatus may be corroded. Moreover, even if the odor can be reduced, the fall in pH cannot be suppressed.

If hydrogenation treatment is performed, heavy metal catalysts such as palladium and nickel are required, but as these catalysts cannot be removed by filtration, heavy metal catalysts may remain in the composition and are therefore unsuitable for use in cosmetics.

As a result of intensive studies to resolve the above disadvantage, the Inventor found that in a composition comprising a crosslinking type organopolysiloxane polymer wherein the crosslinks are formed by hydrophilic organic groups (polyoxyalkylene chains) and a liquid oil, a composition with good storage stability and which did not emit an unpleasant odor could be obtained by adding an acidic substance to this polymer, performing heat treatment, neutralizing with a basic substance and removing volatile components, and thereby arrived at the present invention.

It is therefore an object of this invention to provide a paste-like composition comprising a crosslinking type organopolysiloxane polymer and an oil which has an emulsifying function, which has excellent storage stability and does not emit an unpleasant odor, to provide a method of manufacturing same, and to provide a cosmetic material containing this composition.

SUMMARY OF THE INVENTION

This invention is a paste-like composition obtained by adding at least one acidic substance selected from a group comprising an organic acid, phosphoric acid and phosphate to a mixture comprising a crosslinking type organopolysiloxane polymer wherein the crosslinks are formed by polyoxyalkylene chains and a liquid oil, adding a basic neutralizer so that the pH is 5-8, and removing volatile components by heating and/or reduced pressure, this paste-like composition being characterized in that the amount of propionaldehyde generated when an identical amount of water is added to this composition and heated at 60° C. for 24 hours, is 100 ppm or less.

Herein, the mixture comprising the crosslinking type organopolysiloxane polymer and the liquid oil includes a mixture comprising the crosslinking type organopolysiloxane polymer and liquid oil are simply mixed together, and a mixture wherein the crosslinking type organopolysiloxane polymer and the liquid oil are kneaded together.

This invention is also a method of manufacturing a paste-like composition obtained by adding at least one acidic substance selected from a group comprising an organic acid, phosphoric acid and phosphate to a mixture comprising a crosslinking type organopolysiloxane polymer wherein the crosslinks are formed by polyoxyalkylene chains and a liquid oil, adding a basic neutralizer so that pH is 5-8, and removing volatile components by heating and/or reduced pressure, this method of manufacturing the paste-like composition being characterized in that the amount of propionaldehyde generated when an identical amount of water is added to this composition and heated at 60° C. for 24 hours, is 100 ppm or less.

The salt produced by the acidic substance and the basic neutralizer preferably has a buffer effect, the acidic substance being at least one moiety selected from a group comprising citric acid, lactic acid, malic acid, glutamic acid, tartaric acid, acetic acid, glycine, succinic acid and potassium dihydrogen phosphate, and the basic neutralizer being at least one moiety selected from a group comprising sodium carbonate, sodium hydrogen carbonate, sodium hydroxide, potassium hydroxide, disodium hydrogen phosphate and sodium acetate. The proportions of the acidic substance and basic neutralizer are 0.01-10 wt parts relative to 100 wt parts of the crosslinking type organopolysiloxane, respectively, and preferably, heating is performed to 20-150° C. after adding the acidic substance, and heating is performed to 20-150° C. after adding the basic neutralizer.

The crosslinking type organopolysiloxane polymer is obtained by addition polymerization of at least one moiety selected from a group comprising organohydrogenpolysiloxanes expressed by the following general formula (A1) and the following general formula (A2), and at least one moiety selected from a group comprising unsaturated compounds expressed by the following general formulae (B1), (B2), (B3), and preferably, the crosslinking type organopolysiloxane polymer is insoluble in organic solvents, and can be made to swell up by including at least its own weight of decamethyl cyclopentasiloxane.

  (A1)

  (A2)

  (B1)

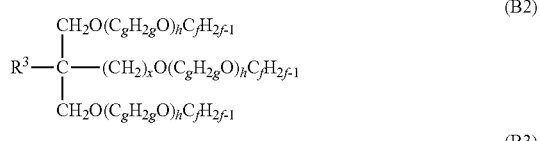  (B2)

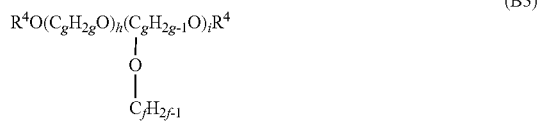  (B3)

In these formulae, $R^1$ are monofunctional hydrocarbon groups which may be respectively identical or different, maybe substituted or unsubstituted, have 1-30 carbon atoms and do not contain an alkenyl group. $R^2$ are organic groups which may identical or different, and are expressed by the general formula —$C_fH_{2f}O(C_gH_{2g}O)_hR^6$.

$R^3$ is a hydrogen atom, or a monofunctional hydrocarbon group having 1-10 carbon atoms which may or may not be substituted, and which does not contain an alkenyl group. $R^4$ are organic groups which are respectively identical or different, identical to $R^3$ or expressed by —$C_fH_{2f-1}$, and $R^6$ is a hydrogen atom, or a monofunctional hydrocarbon group not containing an aliphatic unsaturated group which may or may not be substituted, or an acetyl group.

a, b, c, d, e, are 1.0<a<2.3, 0.001<b<1.0, 0.001<c<1.0, 1.0<d<2.3, and 0.001<e<1.0, respectively, and are positive integers satisfying the relations 1.5<a+b+c<2.6 and 1.5<d<2.6.

f is an integer from 2-6, g is an integer from 2-4, h is an integer from 1-200, i is an integer from 1-20, and x is 0 or 1.

It is particularly preferred that this crosslinking type organopolysiloxane polymer is a polymer comprising the organohydrogen polysiloxane (A2) and polyoxyalkylene (B1).

DESCRIPTION OF THE PREFERRED EMBODIMENTS

Hereafter, this invention will be described in more detail.

The component (A1) is expressed by the average empirical formula $R^1_aR^2_bH_cSiO_{(4-a-b-c)/2}$. In the formula, $R^1$ is a monofunctional hydrocarbon group having 1-30 carbon atoms which may be substituted or unsubstituted, and does not contain an alkenyl group. $R^2$ is an organic group expressed by the general formula —$C_fH_{2f}O(C_gH_{2g}O)_hR^6$. a, b, c are positive integers satisfying the relations 1.0≤a≤2.3, 0.001≤b≤1.0, 0.001≤c≤1.0 and 1.5≤a+b+c≤2.6. f is an integer from 2-6, g is an integer from 2-4, h is an integer from 1-200, and $R^6$ is a hydrogen atom, or a monofunctional hydrocarbon group not containing an aliphatic unsaturated group which may or may not be substituted, or an acetyl group.

Examples of $R^1$ are alkyl groups such as methyl, ethyl, propyl, butyl, pentyl, hexyl, heptyl, octyl, nonyl, decyl; saturated alicyclic hydrocarbon groups such as cyclopentyl and cyclohexyl; aryl groups such as phenyl and tolyl; and fluorinated alkyl groups such as trifluoropropyl, nonafluorohexyl and heptadecylfluorodecyl. a is 1.0-2.3, but preferably 1.2-2.1; b is 0.001-1.0, but preferably 0.005-0.5; and c is 0.001-1.0, but preferably 0.005-0.5. If a is less than 1.0, the degree of crosslinking is too high, so the component cannot contain at least its own weight of decamethyl cyclopentasiloxane, whereas if it is more than 2.3, the degree of crosslinking is too low, so it is difficult to form a three-dimensional crosslinked structure. If b is less than 0.001, the hydrophilicity is low, so it is difficult to form a water-in-oil type (W/O) emulsion composition, whereas if it is more than 1.0, the hydrophilicity is too high, and it is again difficult to form a water-in-oil type emulsion composition. If c is less than 0.001, the degree of crosslinking is low, so it is difficult to form a three-dimensional crosslinked structure, whereas if it is more than 1.0, the degree of crosslinking is too high, so the component cannot contain at least its own weight of decamethyl cyclopentasiloxane.

a+b+c is 1.5-2.6, but preferably 1.8-2.2. f is 2-6, but preferably 3-6. g is an integer from 2-4. The component preferably comprises at least one unit selected from among an ethylene oxide unit, a propylene oxide unit and a butylene oxide unit, but is preferably an ethylene oxide unit, or a copolymer comprising an ethylene oxide unit and a propylene oxide unit. h is an integer from 1-200, but preferably 3-100.

Examples of $R^6$ are hydrogen, methyl, ethyl, propyl, butyl, pentyl, hexyl, heptyl, octyl, nonyl, decyl or acetyl, but hydrogen or methyl is preferred.

This organopolysiloxane maybe straight chain, branched or cyclic, but to make the polymerization reaction go smoothly, it is preferably straight chain, or is mainly straight chain containing some branched units.

Component (A2) is expressed by the average empirical formula $R^1_dH_eSiO_{(4-d-e)/2}$. In the formula, $R^1$ is the same as in the case of (A1), and d, e are positive integers satisfying the relations 1.0≤d≤2.3 and 0.001≤e≤1.0.

d is 1.0-2.3, but preferably 1.2-2.1, and e is 0.001-1.0, but preferably 0.005-0.5. If d is less than 1.0, the degree of crosslinking is too high, so the component cannot contain at least its own weight of decamethyl cyclopentasiloxane, and if d is more than 2.3, the degree of crosslinking is too low, so formation of a three-dimensional crosslinked structure is difficult.

If e is less than 0.001, the degree of crosslinking is too low, so formation of a three-dimensional crosslinked structure is difficult. If e is more than 1.0, the degree of crosslinking is too high, so the component cannot contain at least its own weight of decamethyl cyclopentasiloxane.

This organopolysiloxane may be straight chain, branched or cyclic, but to make the polymerization reaction go smoothly, it is preferably straight chain, or is mainly straight chain containing some branched units.

Component (B1) is expressed by the average empirical formula $C_fH_{2f-1}O(C_gH_{2g}O)_hC_fH_{2f-1}$.

f, g, h in the formula have an identical significance to the above.

Component (B2) is expressed by the average empirical formula:

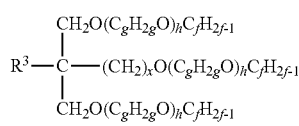

(B2)

In the formula, $R^3$ is a monofunctional hydrocarbon group having 1-10 carbon atoms which may be substituted or unsubstituted, and does not contain unsaturated group bonds. f, g, h are identical to the above, and x is 0 or 1.

Examples of $R^3$ are hydrogen, methyl, ethyl, propyl, butyl, pentyl, hexyl, heptyl, octyl, nonyl and decyl, but hydrogen, methyl, ethyl and propyl are particularly preferred.

Component (B2) can be obtained for example by using glycerol or trimethylolpropane as a starting material, adding an alkylene oxide to this, and performing an alkenyl etheration on the ends of the chain.

All three polyoxyalkylene end groups are alkenyl etherated, but only two maybe sealed by alkenyl etheration and the remaining group left as a hydroxyl group.

If this component (B2) uses glycerol monoallyl ether or trimethylol propane monoallyl ether as starting materials, and after adding an alkylene oxide thereto, the terminal groups are alkenyl etherated, a structure is obtained containing two polyoxyalkylene units in one molecule and three terminal alkenyl groups in one molecule. This polyoxyalkylene compound can also be used.

Component (B3) has the average empirical formula:

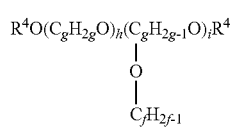

(B3)

In the formula, $R^4$ is identical to $R^3$ or an organic group expressed by $-C_fH_{2f-1}$, f, g, h are identical to those described before, and i is an integer from 1-20.

i is 1-20, but preferably 2-10. If i is more than 20, the degree of crosslinking is too high, so the component cannot contain at least its own weight of decamethylcyclopentasiloxane.

Component (B3) may for example be obtained by adding an alkylene oxide and allyl glycidyl ether to a lower alcohol or allyl alcohol, or after addition, performing alkylation or alkenyl etheration of the terminal.

The crosslinking type organopolysiloxane polymer of this invention can be obtained by carrying out addition polymerization of the organohydrogen polysiloxane expressed by (A1) and/or (A2), and at least one moiety selected from the unsaturated compounds expressed by any of (B1), (B2) and (B3).

Further, to the extent that it does not interfere with the purpose of this invention, addition polymerization can be carried out with the organohydrogen polysiloxane expressed by (A1) and/or (A2) using the organopolysiloxane expressed by the following general formula (B4), or the unsaturated compound expressed by the following general formula (B5).

Component (B4) is expressed by the average empirical formula $R^1_jR^5_kSiO_{(4-j-k)/2}$.

In the formula, $R^1$ is identical to that described before, $R^5$ is a monofunctional hydrocarbon group having 2-10 carbon atoms with a terminal vinyl group, j and k are integers satisfying the relations $1.0 \leq j \leq 2.3$ and $0.001 \leq k \leq 1.0$.

Examples of $R^5$ are vinyl, allyl, butenyl, pentenyl, hexenyl, heptenyl, octenyl, nonenylanddecenyl, butvinyl is preferred.

j is 1.0-2.3, but preferably 1.2-2.1, and k is 0.001-1.0, but preferably 0.005-0.5.

If j is less than 1.0, the degree of crosslinking is too high, so the component will be unable to contain at least its own weight of decamethyl cycloheptasiloxane, whereas if j is larger than 2.3, the degree of crosslinking is too low, so formation of a three-dimensional structure is difficult.

If k is less than 0.001, the degree of crosslinking is too low, so formation of a three-dimensional structure is difficult, whereas if k is larger than 1.0, the degree of crosslinking is too high, so the component will be unable to contain at least its own weight of decamethyl cycloheptasiloxane.

This organopolysiloxanemaybe straight chain, branched or cyclic, but to make the polymerization reaction go smoothly, it is preferably straight chain, or is mainly straight chain containing some branched units.

Component (B5) is expressed by the average empirical formula $C_mH_{2m-1}(CH_2)_yC_mH_{2m-1}$, and m is an integer from 2-6. y is an integer equal to 1 or more, but preferably an integer from 1-10.

If unreacted polyether wherein the double bond of the terminal allyl group has migrated is not present as an impurity in component (A1), ketones and aldehydes which cause odor are not generated even if components (B4) or (B5) are reacted with this component (A1).

For example, if all the polyoxyethylene monoallyl ether is added first to the component (A2) to prepare an intermediate without unsaturated groups by removing the odor of the remaining unreacted polyether with hydrochloric acid or performing a hydrogenation, introducing a source of Si—H by an equilibrium reaction or the like to synthesize the component (A1), and then reacting this with components (B4) or (B5); or if part of the polyoxyethylene monoallyl ether is added to component (A2), and the remaining polyether is treated by removing the odor with hydrochloric acid or by hydrogenation to synthesize the component (A1) without unsaturated groups, which is then reacted with components (B4) or (B5), a crosslinked product can be obtained even without the processing steps of the invention. However, in practice, if part of the polyoxyethylene monoallyl ether is added to component (A2), a crosslinked product might be obtained by reacting components (B4) or (B5) without removing the remaining unsaturated groups. In this case, writing a general equation, the stage where the polyether is partially added corresponds to component (A1), and as unreacted polyether containing unsaturated groups is present, the crosslinked product obtained by reaction of components (B4) or (B5) will generate an unpleasant odor. Therefore, to the extent that the purpose of this invention is not lost, a polymer within the scope of this invention can be obtained not only by using components (B4) and/or (B5) in conjunction with the unsaturated compounds expressed by (B1), (B2), (B3), but also by crosslinking components (B4) and/or (B5) alone.

The crosslinking type organopolysiloxane polymer of this invention obtained by the aforesaid addition polymerization is an organopolysiloxane polymer wherein the organopolysiloxane structure is crosslinked by the polyoxyalkylene chains. Moreover, a paste-like composition can be obtained by kneading the organopolysiloxane addition polymer obtained in this way with a liquid oil. This paste-like composition may also be obtained by manufacturing an organic polysiloxane polymer by the addition polymerization of the organohydrogen polysiloxane expressed by (A1) and/or (A2) with a mixture comprising the polyoxyalkylene expressed by (B1), (B2) or (B3), and as arbitrary components, the organic polysiloxane expressed by (B4) and at least one moiety selected from among unsaturated compounds expressed by (B5), and part of the liquid oil, and then kneading this organopolysiloxane polymer with the remaining liquid oil.

Another method of obtaining the paste-like organopolysiloxane composition of this invention is to first purify the addition polymer, and then mix and knead it with the liquid oil. It may also be obtained by purifying the addition polymer while still containing the organic solvent used for the reaction, mixing with the liquid oil after removing volatile components such as the solvent and odorous components, and kneading. However, even if an aqueous solution of an organic acid is added to an addition polymer which does not contain liquid oil, as the efficiency of contact with the treatment solution is low, it is difficult to improve the degree of purity and perform a neutralization reaction.

To obtain the organopolysiloxane polymer of this invention, the reaction may be performed in the presence of a platinum compound (for example, chloroplatinic acid, alcohol-modified chloroplatinic acid or chloroplatinic acid-vinyl siloxane complex), or a rhodium compound, at room temperature or by heating (about 50-120° C.). The reaction may be performed without a solvent, or an organic solvent may be used if required. Examples of such organic solvents are aliphatic alcohols such as methanol, ethanol, 2-propanol and butanol; aromatic hydrocarbons such as benzene, toluene and xylene; aliphatic or alicyclic hydrocarbons such as n-pentane, n-hexane and cyclohexane; halogenated hydrocarbons such as dichloromethane, chloroform and carbon tetrachloride; and ketone solvents such as acetone and methyl ethyl ketone. However, in order to widen application as a cosmetic material, no solvent, or ethanol or 2-propanol are preferred.

In this addition reaction, the same problem as was already pointed out in Tokko Hei 07-91389 and Tokkai Hei 07-330907 occurs. Specifically, a part of the polyoxyalkylene of (B1)-(B3) causes an internal rearrangement according to a side reaction based on the action of the platinum catalyst, and remains without reacting with the —SiH group of the organohydrogen polysiloxane of (A1) and (A2).

For example, when an allyl etherated polyoxyalkylene is used as the polyoxyalkylene, the allyl group undergoes an internal rearrangement as a side reaction, and propenyl etherated polyoxyalkylene is produced. This propenyl etherated polyoxyalkylene remains without undergoing an addition reaction with the —SiH group, decomposing with time to generate ketones and aldehydes which are responsible for odor.

The organopolysiloxane addition polymer of this invention has a three-dimensional crosslinkage which is insoluble in organic solvents, the organic solvents mentioned here being aliphatic organic solvents such as straight chain or branched pentane, hexane, decane, dodecane, hexadecane and octadecane, aromatic organic solvents such as benzene, toluene and xylene, alcoholic organic solvents such as methanol, ethanol, propanol, butanol, hexanol and decanol, halogenated organic solvents such as chloroform and carbon tetrachloride, ketoneorganic solvents such as acetone and methyl ethyl ketone, and silicone solvents such as low viscosity dimethylpolysiloxane, ethylphenylpolysiloxane and cyclic dimethylpolysiloxane.

The organopolysiloxane addition polymer of this invention is characterized by swelling with at least its own weight of decamethylcyclopentasiloxane, and this can be confirmed as follows.

Equal weights of the organopolysiloxane addition polymer and decamethyl cyclopentasiloxane are mixed, and allowed to stand at room temperature. After standing, it is verified that there is no separation of decamethylcyclopentasiloxane even if the sample is placed on a 100 mesh sieve and left for 5 minutes.

In manufacturing the silicone composition of this invention, kneading of the organopolysiloxane addition polymer and liquid oil may be performed by an ordinary stirrer, but this is preferably performed under a shear force. This is because, as the organopolysiloxane addition polymer has a three-dimensional crosslinked structure which is insoluble in solvents, a paste-like composition of smooth appearance is obtained by giving sufficient dispersibility to the organopolysiloxane addition polymer and liquid oil.

The kneading can be performed by, for example, a three-roll mill, two-roll mill, side grinder, colloidal mill, Gaulin homogenizer or disper, but a three-roll mill or disper are particularly preferred.

The liquid oil used in this invention may be suitably selected from among those demonstrating fluidity at 25° C. Examples are silicone oil, hydrocarbon oil, ester oil, natural animal and vegetable oils and semi-synthetic oil.

As examples of other silicone oils which can be mixed, mention maybe made of organopolysiloxanes having from low to high viscosities, such as dimethylpolysiloxane, methylphenylpolysiloxane, and dimethylsiloxane-methylphenylsiloxane copolymer; cyclic siloxanes, such as octamethylcyclotetrasiloxane, decamethylcyclopentasiloxane, dodecamethylcyclohexasiloxane, tetramethyltetraphenylcyclotetrasiloxane; branched siloxanes such as tristrimethyl siloxymethylsilane and tetrakistrimethylsiloxysilane, silicone gum, such as gummy dimethylpolysiloxanes having high polymerization degrees and gummy dimethylsiloxane-methylphenylsiloxane copolymers having high polymerization degrees; and cyclosiloxane solutions of silicone gum.

Examples of hydrocarbon oils are straight chain or branched volatile hydrocarbon oils, specifically, alpha-olefin oligomers, light isoparaffin, light flowing isoparaffin, squalane, synthetic squalane, vegetable squalane, squalene, liquid paraffin and liquid isoparaffin.

Examples of an ester oil which can be mixed therein include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropylmyristate, octyldodecylmyristate, 2-hexyldecyl myristate, myristyl myristate, hexyldecyl dimethyloctanoate, ethyl laurate, hexyl laurate, N-lauroyl-L-glutaminic acid 2-octyldodecyl ester and diisostearyl malic acid.

Examples of ester oil which are glyceride oils are acetoglyceryl, glyceryl trioctanoate, glyceryl triisostearate, glyceryl triisopalmitate, glyceryl monostearate, glyceryl di-2-heptyl undecanoate, glyceryl trimyristate and diglyceryl myristate-isostearate.

Examples of higher fatty acids are undecylenic acid, oleic acid, linolic acid, linolenic acid, arachidonic acid, eicosapentaenoic acid (EPA), docosa-hexaenoic acid (DHA), isostearic acid and lactic acid, and examples of higher alcohols are oleyl alcohol, isostearyl alcohol, hexyl decanol, octyl dodecanol, cetostearyl alcohol, 2-decyltetradecinol and monooleyl glyceryl ether (selachyl alcohol).

Examples of natural animal and vegetable oils and fats, and semi-synthetic oils and fats, are avocado oil, almond oil, olive oil, liver oil, beef foot tallow, apricot kernel oil, wheat germ oil, sesame oil, rice germ oil, rice bran oil, sasanqua oil, safflower oil, cinnamon oil, turtle oil, soybean oil, tea fruit oil, camellia oil, eveningprimrose oil, corn oil, rapeseed oil, Japanese kiri oil, germ oil, par chic oil, castor oil, castor oil fatty acid methylester, sunflower seed oil, grape oil, jojoba oil, macadamia nut oil, mink oil, medoform oil, cotton seed oil, tricoconut oil fatty acid glycerides, arachis oil, liquefied lanolin, acetic acid lanolin alcohol, lanolin fatty acid polyethylene glycol and egg yolk oil.

The blending proportion of the organopolysiloxane polymer crosslinked by the aforesaid polyoxyalkylene chains and liquid oil is preferably 1/20-20/1 (weight ratio), but more preferably 1/10-1/1.

The addition amount of acidic substance is 0.01-10 wt parts, but preferably 0.02-5 wt parts, relative to 100 wt parts of the crosslinking type organopolysiloxane polymer crosslinked by polyoxyalkylene chains. If it is less than 0.01 wt parts, the odor removal effect is poor, and if it is more than 10 wt parts, neutral salts separate from the composition after treatment which is undesirable. These organic acids may be added as they are, but it is preferred to add them as a 1-50% aqueous solution.

The pasty composition comprising the crosslinking type polyoxyalkylene compound crosslinked by polyoxyethylene chains and liquid oil may also be prepared, and treated by adding an acidic substance to this pasty composition. As for treatment conditions after adding the acidic substance, heating is unnecessary, but heating may be performed to 20-150° C., and preferably 50-100° C.

The basic neutralizing agent may be added as it is, but it is preferably added as a 1-50% aqueous solution. The addition amount is adjusted so that the functional group equivalent of the aforesaid acidic substance and basic neutralizing agent is 1/0.1-0.1/1, but preferably 1/0.3-0.3/1, and the acidity or alkanility after neutralization is 5-8.

The treatment conditions after addition of the basic neutralizing agent are 20-150° C., but preferably 20-80° C.

Examples of the acidic substance are citric acid, lactic acid, tartaric acid, malic acid, glutamic acid, acetic acid, glycine, potassium dihydrogenphosphate and succinic acid, but citric acid, lactic acid, and glutamic acid are preferred.

Examples of the basic neutralizer are sodium carbonate, sodium hydrogen carbonate, sodium hydroxide, potassium hydroxide, disodium hydrogen phosphate and sodium acetate, but sodium carbonate, sodium hydrogen carbonate and sodium hydroxide are preferred.

By selecting this acidic substance and basic neutralizer from mixtures such that the salt produced by neutralization has a pH buffer effect, not only is the odor reduced, but the pH of the composition can be stabilized.

This invention is a cosmetic material formed by blending any of the aforesaid pasty compositions. This cosmetic material may comprise at least one moiety selected from a group comprising (C) water, (D) a compound having an alcoholic hydroxyl group in the molecule, (E) a water-soluble or water-swelling polymer, (F) a powder and/or colorant, (G) a surfactant, (H) a composition comprising a non-hydrophilic crosslinking type organopolysiloxane compound and liquid oil, and (I) a silicone resin.

At least part of (F), the powder and/or colorant, is preferably a crosslinking type spherical silicone fine powder having a structure wherein dimethylpolysiloxane is crosslinked, a crosslinking type spherical polymethylsilsesquioxane fine powder, or a fine powder obtained by coating across linking type spherical silicone rubber surface with polymethylsilsesquioxane particles.

Afore mentioned (G), the surfactant, is preferably a straight-chain or branched silicone having a polyoxyalkylene chain in the molecule, and more preferably, its HLB is 2-8.

The aforesaid (I) silicone resin is preferably an acrylic silicone resin, and is more preferably a silicone resin having at least one organic group selected from among a pyrrolidone group, long chain alkyl group, polyoxyalkylene group, fluoroalkyl group and anionic carboxyl group in the molecule. In particular, it is at least one type of silicone resin selected from resins comprising a $R^1_3SiO_{0.5}$ unit and $SiO_2$ unit, resins comprising a $R^1_3SiO_{0.5}$ unit, $R^1_2SiO$ unit and $SiO_2$ unit, resins comprising a $R^1_3SiO_{0.5}$ unit and $R^1SiO_{1.5}$ unit, resins comprising a $R^1_3SiO_{0.5}$ unit, $R^1_2SiO$ unit and $R^1SiO_{1.5}$ unit, and resins comprising a $R^1_3SiO_{0.5}$ unit, $R^1_2SiO$ unit, $R^1SiO_{1.5}$ unit and $SiO_2$ unit, but among these, silicone resins comprising at least one organic group selected from among a pyrrolidone group, long chain alkyl group, polyoxyalkylene group, fluoroalkyl group and anionic group of a carboxyl group are preferred.

(C), water, can also be blended with the cosmetic material of this invention according to the purpose. The blending amount may conveniently be within the range of 1-95% of the total weight of cosmetic material.

In the cosmetic material of this invention, one,(D) two or more compounds having an alcoholic hydroxyl group in the molecular structure may be used according to the purpose. Examples of compounds having an alcoholic hydroxyl group which can be added in this invention are lower alcohols such as ethanol and isopropanol, sugar alcohols such as sorbitol and maltose, and sterol such as cholesterol, sitosterol, phytosterol, lanosterol, polyhydric alcohols such as butylene glycol, propylene glycol and dibutylene glycol, but normally, water-soluble monohydric alcohols and water-soluble polyhydric alcohols are used.

The blending proportion of component (D) may conveniently be 0.1-98% of the total weight of the cosmetic material.

In the cosmetic material of this invention, one, two or more of (E) water-soluble or water-swelling polymers can also be used according to the purpose. Examples of these polymers are: plant polymers such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulosepolymers, suchasmethyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride.

Film-forming agents, such as polyvinyl alcohol and polyvinyl pyrrolidone, are also contained in these water-soluble polymers. The blending amount of component (E) is conveniently within the range of 0.1-25 wt % of the total cosmetic material.

In the cosmetic material of this invention, one, two or more of the powder and/or colorant (F) may also be used according to the purpose.

If the powder is used in ordinary cosmetic materials, it maybe used regardless of its shape (spherical, acicular, plate), particle diameter (fume, fine particles or pigment grade), or particle structure (porous, non-porous). Such powders may for example be inorganic fine particles, organic fine particles, surfactant metal salt fine particles, a colored pigment, a pearl pigment, a metal powder pigment or natural coloring matter.

Examples of inorganic fine particles are titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, syntheticmica, phlogopite, redmica, biotite, lithiamica, silicic acid, silicic acid anhydride, aluminium silicate, magnesium silicate, magnesium aluminium silicate, calcium silicate, barium silicate, strontium silicate, tungstic acid metal salts, hydroxyapatite, vermiculite, haidilite, bentonite, montmorillonite, hectorite, zeolite, ceramic powder, dibasic calcium phosphate, alumina, aluminium hydroxide, boron nitride, boron nitride and silica.

Examples of organic fine particles are polyamide powder, polyester powder, polyethylene powder, polypropylene powder, polystyrene powder, polyurethane, benzoguanamine powder, polymethyl benzoguanamine powder, tetrafluoroethylene powder, polymethylmethacrylate powder, cellulose, silk powder, nylon powder, 12 nylon, 6 nylon, crosslinking type silicone fine powder having a structure wherein dimethylsilicone is crosslinked, polymethylsilsesquioxane fine powder, styrene-acrylic acid copolymer, divinylbenzene styrene copolymer, vinyl resin, urea resin, phenol resin, fluoroesin, silicon resin, acrylate resin, melamine resin, epoxy resin, polycarbonate resin, microcrystalline fiber fine particles, starch powder and lauroyl lysine.

Examples of surfactant metal salt fine particles (metal soap) are zinc stearate, aluminum stearate, calcium stearate, magnesium stearate, zinc myristate, magnesium myristate, zinc cetyl phosphate, calcium cetyl phosphate and zinc sodium cetyl phosphate.

Examples of colored pigments are inorganic red pigments such as iron oxide, iron hydroxide and iron titanate, inorganic brown pigments such as γ-iron oxide, inorganic yellow pigments such as yellow iron oxide and ocher, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as Berlin blue and ultramarine blue, tar pigment lake, natural pigment lake and synthetic resin powders which are complexes of these powders.

Examples of pearl pigments are titanium oxide-coated mica and titanium oxide-coated mica, bismuth oxychloride, titanium oxide-coated bismuth oxychloride, titanium oxide-coated talc, scales foil and titanium oxide-coated colored mica; examples of metal powder pigments are aluminium powder, copper powder and stainless steel powder.

Examples of tar dyes are Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; examples of natural pigments are powders selected from among carminic acid, laccainic acid, carthamin, bradilin and crocin.

Of these powders and/or colorants, those wherein at least part is a crosslinking type silicone fine powder having a structure wherein dimethylsilicone is crosslinked, polymethylsilsesquioxane fine powder, hydrophobic silica, or a composite fine powder wherein a spherical silicone rubber surface is coated by polymethylsilsesquioxane particles, or those wherein at least part of the powder and/or colorant has a fluorine group, are often used. Further, to the extent that it does not interfere with the effect of this invention, composite powders or those which have been treated with ordinary oils, silicone oil, fluorine compounds or surfactants may be used, one, two or more of these being used as required. The blending proportion is conveniently within the range of 0.1-99 wt % of the total cosmetic material. In particular, the blending proportion in a powder solidified cosmetic material is conveniently within the range of 80-99 wt % of the total cosmetic material.

The cosmetic material of this invention may also use one, two or more of the surfactants (G) according to the purpose. The surfactants may be anionic, cationic, non-ionic or amphoteric active agents and are not particularly limited, and any of those used in ordinary cosmetic materials may be used herein.

Examples of a usable anionic surfactant include fatty acid soap, such as sodium stearate or triethanolamine palmitate;

alkyl ether carboxylic acids and salts thereof; salts of amino acid-fatty acid condensates; alkanesulfonates; alkenesulfonates; sulfonatedfattyacid esters; sulfonated fatty acid amides; sulfonates of formaldehyde condensate type; alkylsulfates; higher secondary alcohol sulfates; alkyl and aryl ether sulfates; fatty acid ether sulfates, fatty acid alkylolamide sulfates; ether sulfates such as Turkey red oil; alkyl phosphates; ether phosphates; alkyl aryl ether phosphates; amide phosphates; and active agents of N-acylaminoacid type; examples of a usable cationic surfactant include amine salts, such as alkylamine salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerinfattyacidesters, propyleneglycolfattyacid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ehter, polyoxyethylene phytosterol ether, polyoxyethylene cholestanol ether, polyoxyethylene cholesteryl ether, polyoxyalkylene-modified organopoly-siloxanes, organopolysiloxanes modified with both polyoxyalkylene and alkyl groups, alkanolamides, sugar ethers and sugar amides; and examples of a usable amphoteric surfactant include betaine, aminocarboxylate, imidazoline derivatives and amidoamines.

Of these surfactants, surfactants which are straight-chain or branched organopolysiloxane having a polyoxyalkylene chain in the molecule, and surfactants whereof the HLB is 2-8, are often used.

The blending proportion of the component (G) is preferably in the range of 1-20 wt %, but more preferably 0.2-10 wt %, of the total cosmetic material.

In the cosmetic material of this invention, one, two or more crosslinking type organopolysiloxanes which do not contain a polyoxyalkylene chain which swells up when it contains a low viscosity organopolysiloxane of from 0.65mm$^2$/s (25° C.) to 100.0 mm$^2$/s (25° C.) in an amount larger than its own weight, may also be used as the component (H) according to the purpose. This crosslinking type organopolysiloxane preferably swells up with at least its own weight of the low viscosity organopolysiloxane relative to the low viscosity organopolysiloxane of from 0.65 mm$^2$/s (25° C.) to 100.0 mm$^2$/s (25° C.). The blending amount of this crosslinking type organopolysiloxane is preferably 0.1-50 wt % but more preferably 1-30 wt %, of the total amount of cosmetic material. These are not limiting, but examples are the organopolysiloxane composition described in Tokkyo 1925781, the organopolysiloxane polymer described in the same patent, or a composition comprising an oil other than the organopolysiloxane oil.

One, two or more of the silicone resins (I) can also be used for the cosmetic material of this invention according to the purpose, This silicone resin is preferably an acrylic/silicone graft resin or block copolymer acrylic silicone resin. An acrylic silicone resin comprising at least one moeity in the molecule selected from among pyrrolidone, long chain alkyl, polyoxyalkylene, fluoroalkyl and anions such as carboxylic acid, can also be used.

Further, this silicone resin is preferably a silicone reticular compound represented by MQ, MDQ, MT, MDT or MDTQ as a constituent component. This M, D, T, and Q, respectively express $R_3SiO_{0.5}$ unit, $R_2SiO$ unit, $RSiO_{1.5}$ unit or $SiO_2$ unit, and are commonly used in the silicone industry. A silicone reticular compound containing at least one moiety in the molecule selected from among pyrrolidone, long chain alkyl, polyoxyalkylene, fluoroalkyl and amino can also be used.

The blending amount of the silicone resin which is the component (I), such as an acrylic silicone resin or a silicone reticular compound, is preferably 0.1-20 wt %, but more preferably 1-10 wt %, relative to the total amount of cosmetic material.

To the present cosmetic material, the ingredients used in general cosmetic materials, such as an oil-soluble gelling agent, clay minerals modified with organic compounds, resins,antiperspiration, ultraviolet absorbents, an ultraviolet absorption and scattering agent, a moisture-holding agent, antiseptics, an antimicrobial agent, perfume, salts, antioxidants, pH regulators, a chelating agent, refrigerant, an anti-inflammatory agent, skin beautifying components (a skin whitener, a cell activator, a rough dry skin improver, a blood circulation promoter, a skin astringent and an anti-seborrheic agent), vitamins, aminoacids, nucleic acids, hormones, clathrate compounds and hair firming agents can be added so far as they have no adverse influence on the effects of the present invention.

Examples of an oil-soluble gelling agent which can be added include metal soaps, such as aluminum stearate, magnesium stearate and zinc myristate; aminoacid derivatives, such as N-lauroyl-L-glutamic acid and α, γ-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of an antiperspirant which can be added may be selected from among aluminum chlorohydrate, aluminum chloride, aluminum sesquichlorohydrate, zirconyl hydroxychloride, aluminum zirconium hydroxychloride and aluminum zirconium glycine complex.

Examples of an ultraviolet absorbent which can be added include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of an ultraviolet absorption and scattering agent which can be added are powders which absorb and scatter ultraviolet light such as fine particle titanium oxide, fine particle iron-containing titanium oxide, fine particle zinc oxide, fine particle cerium oxide and their complexes.

Examples of a moisture-holding agent which can be added include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylic acid, polyoxyethylene glycoside, and polyoxypropylene methylglycoside.

Examples of preservatives which can be added include alkyl p-oxybenzoates, benzoic acid, sodium benzoate, sorbic acid, potassium sorbate and phenoxyethanol; and those of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitizer and phenoxyethanol.

Examples of an antioxidant which can be added include tocopherol, butylhydroxyanisole, dibutylhydroxytoluene and phytic acid; those of a pH regulator which can be added include lactic acid, citric acid, glycolic acid, succinic acid, tartaric acid, dl-malic acid, potassium carbonate, sodium hydrogen carbonate and ammonium hydrogen carbonate; those of a chelating agent which can be added include alanine, sodium ethylenediaminetetraacetate, sodium polyphosphate, sodium metaphosphate and phosphoric acid; those of a refrigerant which can be added include L-menthol and camphor; and those of an anti-inflammatory agent which can added include allantoin, glycyrrhizin and salts thereof, glycyrrhetinic acid and stearyl glycyrrhetinate, tranexamic acid and azulene.

Examples of a skin-beautifying component which can be added include whitening agents, such as placenta extract, arbutin, glutathione and Yukinoshita extract; cell activators, such as royal jelly, photosensitizer, cholesterol derivatives and calf blood extract; rough dry skin improvers; blood circulation improvers, such as nonylic acid vanillyl amide, benzyl nicotinate, β-butoxyethylnicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and anti-seborrheic agents, such as sulfur and thianthol.

Examples of vitamins which can be added include vitamin A, such as vitamin A oil, retinol, retinyl acetate and retinyl palmitate; vitamin B, including vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitaminE, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an aminoacid which can be added include glycine, valine, leucine, isoleucine, serine, threonine, phenylaranine, alginine, lysine, aspartic acid, glutamic acid, cystine, cysteine, methionine, and tryptophan; those of a nucleic acid which can be added include deoxyribonucleic acid; and those of a hormone which can be added include estradiol and ethenyl estradiol.

Examples of a hair firming polymer compound are amphoteric, anionic, cationic or nonionic polymer compounds, e.g., polyvinyl pyrrolidone-polymer compounds such as polyvinyl pyrrolidone and vinyl pyrrolidone/vinyl acetate copolymer, acidic vinyl ether polymer compounds such as methyl vinyl ether/maleic anhydride alkyl half ester copolymer, acidic polyvinyl acetate-polymers such as vinyl acetate/crotonic acid copolymer, acidic acrylic polymer compounds such as (meth)acrylic acid/alkyl(meth)acrylate copolymer and (meth)acrylic acid/alkyl (meth) acrylate/alkyl acrylamide copolymer, and amphoteric acrylic-polymer compounds such as N-methacryloylethyl-N,N-dimethyl ammonium-alpha-N-methyl carboxy betaine/alkyl(meth)acrylate copolymer, hydroxypropyl(meth)acrylate/butylaminoethylmethacrylat e/acrylic acid octylamide copolymer. Also, naturally-occurring polymer compounds such as cellulose or its derivatives, keratin, and collagen or its derivatives, can also be used.

Examples of a higher alcohol which can be mixed therein include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

As examples of other silicone oils which can be mixed, mention may be made of higher alkoxy-modified silicones such as stearoxysilicone, higher fatty acid-modified silicones, alkyl-modified silicones, amino-modified silicones and fluorine-modified silicones.

Examples of fluorinated oils are fluoropolyether, perfluorodecalin and perfluorooctane.

The "cosmetic material" of this invention formed by blending the aforesaid cosmetic material components may be a skincare product such as a milky lotion, cream, face cleansing cream, packs, oily liquid, massage material, rinsing agent, deodorants, hand creamor lip cream; a makeup product such as a foundation, powder, liquid foundation, oily foundation, rouge, eye shadow, mascara, eyeliner, eyebrow, makeup such as lipstick; a hairdressing product, such as a shampoo, rinse, treatment and set; an antiperspirant, or an ultraviolet defense cosmetic material such as suncut milky lotion or suncut cream.

Additionally, the present cosmetic material may have any form, including liquid, emulsion, cream, solid, paste, gel, powder, compress, layers, mousse, spray or stick.

The oily composition comprising the crosslinking type organopoly siloxane having hydrophilic organic groups which has been purified and liquid oil according to this invention does not easily suffer a drop of pH during long storage or when heated and left, and the unpleasant odor generated over time is largely suppressed even when blended with an emulsion. Therefore, a highly stable cosmetic material may be obtained by the use of this composition.

EXAMPLES

Hereafter, this embodiment will be described by specific examples, but it should be understood that this invention is not limited in any way thereby.

Composition 1.

100.0 g of an organohydrogen polysiloxane expressed by the average formula (1):

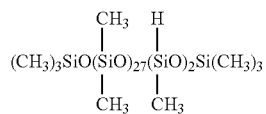
(1)

23.6 g of the polyoxyalkylene compound expressed by the average formula (2), 120.0 g of ethanol and 0.3 g of a 3 wt % ethanol solution of chloroplatinic acid were introduced into a reactor, and stirred for 2 hours while maintaining the internal temperature at 70-80° C. The solvent was removed under reducedpressure, and the organopolysiloxane addition polymer (P1) was obtained.

$$CH_2=CHCH_2O(C_2H_4O)_{10}CH_2CH=CH_2 \quad (2)$$

30 wt parts of the obtained organopolysiloxane addition polymer (P1) and 70 wt parts of a dimethylpolysiloxane having a viscosity of 10 mm$^2$/s at 25° C., were mixed and dispersed, and kneaded by a three roll mill to obtain a pasty composition (C1).

Composition 2.

100.0 g of an organohydrogen polysiloxane expressed by the average formula (3):

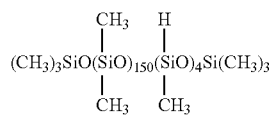
(3)

34.7 g of the polyoxyalkylene compound expressed by the average formula (4), 34.3 g of dimethylpolysiloxane having a viscosity of 20 mm$^2$/s at 25° C., 150.0 g of ethanol and 0.3 g of a 3 wt % ethanol solution of chloroplatinic acid were introduced into a reactor, and stirred for 2 hours while maintaining the internal temperature at 70-80° C. The solvent was removed under reduced pressure, and an organopolysiloxane addition polymer (P2) was obtained.

$$CH_2=CHCH_2O\ (C_2H_4O)_{30}(C_3H_6O)_{10}CH_2CH=CH_2 \quad (4)$$

Next, 25 wt parts of the obtained organopolysiloxane addition polymer (P2) and 75 wt parts of a dimethylpolysiloxane having a viscosity of 20 mm$^2$/s at 25° C., were mixed and dispersed, and kneaded by a three roll mill to obtain a pasty composition (C2).

Composition 3.

323.0 g of an organohydrogen polysiloxane expressed by the average formula (5):

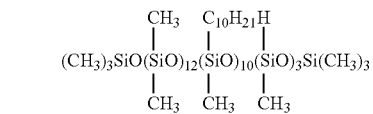
(5)

81.0 g of the polyoxyalkylene compound expressed by the average formula (2), 100.0 g of 2-propanol and 0.3 g of a 3 wt % ethanol solution of chloroplatinic acid were introduced into a reactor, and stirred for 2 hours while maintaining the internal temperature at 70-80° C. The solvent was removed under reduced pressure, and an organopolysiloxane addition polymer (P3) was obtained.

Next, 30 wt parts of this organopolysiloxane addition polymer (P3) and 70 wt parts of a fluid paraffin were mixed and dispersed, and kneaded by a three roll mill to obtain a pasty composition (C3).

Composition 4.

20 wt parts of the organohydrogen polysiloxane (P3) and 80 wt parts of cetyl isooctanoate were mixed and dispersed, and kneaded by a three roll mill to obtain a pasty composition (C4).

Composition 5.

156.3 g of an organohydrogen polysiloxane expressed by the average empirical formula (6):

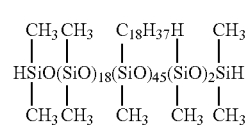
(6)

21.0 g of the polyoxyalkylene compound expressed by the average formula (7), 70.0 g of 2-propanol and 0.1 g of a 3 wt % ethanol solution of chloroplatinic acid were introduced into a reactor, and stirred for 2 hours while maintaining the internal temperature at 70-80° C. The solvent was removed under reduced pressure, and an organopolysiloxane addition polymer (P4) was obtained.

$$CH_2=C(CH_3)CH_2O(C_2H_4O)_{20}CH_2C(CH_3)=CH_2 \quad (7)$$

Next, 30 wt parts of this organopolysiloxane addition polymer (P4) and 70 wt parts of squalane were mixed and dispersed, and kneaded by a three roll mill to obtain a pasty composition (C5).

Composition 6.

30 wt parts of the organohydrogen polysiloxane (P3) and 70wt parts of macadamia nut oil were mixed and dispersed, and kneaded by a three roll mill to obtain a pasty composition (C6).

Composition 7.

676.0 g of an organohydrogen polysiloxane expressed by the average formula (8):

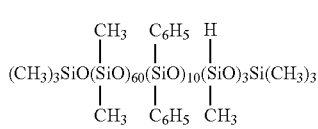

(8)

165.0 g of the polyoxyalkylene compound expressed by the average y formula (9), 300.0 g of 2-propanol and 0.3 g of a 3 wt % ethanol solution of chloroplatinic acid were introduced into a reactor, and stirred for 2 hours while maintaining the internal temperature at 70-80° C. The solvent was removed under reduced pressure, and an organopolysiloxane addition polymer (P5) was obtained.

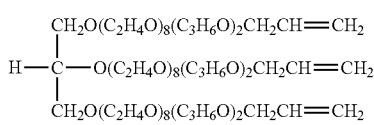

(9)

Next, 30 wt parts of this organopolysiloxane addition polymer (P5) and 70 wt parts of glyceryl trioctanoate were mixed and dispersed, and kneaded by a three roll mill to obtain a pasty composition (C7).

Composition 8.

368.0 g of an organohydrogen polysiloxane expressed by the average formula (10):

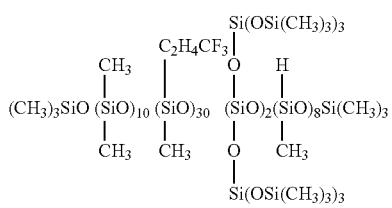

(10)

100.0 g of the polyoxyalkylene compound expressed by the average formula (11) and 0.3 g of a 3 wt % ethanol solution of chloroplatinic acid were introduced into a reactor, and stirred for 2 hours while maintaining the internal temperature at 70-80° C. The solvent was removed under reduced pressure, and an organopolysiloxane addition polymer (P6) was obtained.

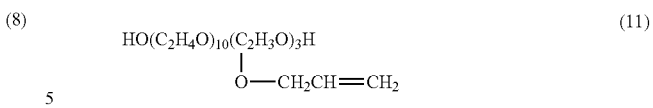

(11)

Next, 30 wt parts of this organopolysiloxane addition polymer (P6) and 70 wt parts of the fluorinated organopolysiloxane (viscosity 100 mm²/s) expressed by (12) were mixed and dispersed, and kneaded by a three roll mill to obtain a pasty composition (C8).

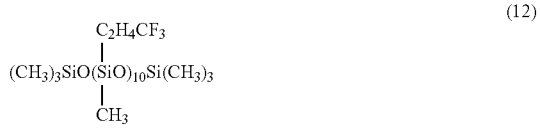

(12)

Examples 1-5

A refining treatment was performed under the following conditions using the compositions shown in Table 1 using the pasty composition C1.

First, the 2% organic acid aqueous solution (10 g) was added to the pasty composition C1 (100 g), and thoroughly mixed. Next, the internal temperature was maintained at 70-80° C., and mixing and heat-treatment was performed for 3 hours. Cooling was performed until the internal temperature reached 50° C. or less, a predetermined amount of 5% sodium hydrogen carbonate aqueous solution was added, the internal temperature was maintained at 40-50° C., and stirring was performed for 1 hour. After stirring was complete, the internal temperature was raised to 100° C. under reduced pressure, and volatile components were removed to obtain the target substance.

Comparative Example 1

The target substance was obtained without performing the refining treatment of this invention on the pasty composition.

Comparative Example 2 (Method Disclosed in Tokkai Hei 07-91389)

10 g (reference is 6 g) of $10^{-2}$N (reference is $10^{-3}$N) aqueous hydrochloric acid was added to the pasty composition C1 (100 g), and stirring was performed at 90° C. for 4 hours.

After performing a reduced pressure strip, purification filtration was performed to obtain the target substance.

TABLE 1

|  | Ex. 1 | Ex. 2 | Ex. 3 | Ex. 4 | Ex. 5 | Comp Ex. 1 | Comp. Ex. 2 |
|---|---|---|---|---|---|---|---|
| Pasty composition C1 | 100.0 | 100.0 | 100.0 | 100.0 | 100.0 | 100.0 | 100.0 |
| 2% aqueous succinic acid solution | 10.40 | 0 | 0 | 0 | 0 | 0 | 0 |
| 2% aqueous lactic acid solution | 0 | 10.0 | 0 | 0 | 0 | 0 | 0 |
| 2% aqueous maleic acid solution | 0 | 0 | 10.0 | 0 | 0 | 0 | 0 |
| 2% aqueous tartaric acid solution | 0 | 0 | 0 | 10.0 | 0 | 0 | 0 |
| 2% aqueous glutamic acid solution | 0 | 0 | 0 | 0 | 10.0 | 0 | 0 |
| 0.01 N aqueous hydrochloric acid | 40 | 0 | 0 | 0 | 0 | 0 | 10.0 |
| 5% aqueous sodium hydrogen carbonate | 3.5 | 3.7 | 2.5 | 2.2 | 2.3 | 0 | 0 |
| Propionaldehyde production amount (ppm) | 10.0 | 12.1 | 25.2 | 17.6 | 21.3 | 750 | 11.4 |

Propionaldehyde Production Test 5 g of purified composition and 5 g of water were mixed, introduced into a special 20 ml container, sealed, and heated at 60° C. for 24 hours. A headspace gas chromatography analysis was performed, and the amount of propionaldehyde generated was measured. As a result, it was found that in the case of the examples as compared to Comparative Example 1, the unpleasant odor very much decreased.

pH Value Measurement Test 10 g of the aforesaid treated product was taken up in a 100 ml glass bottle, and heated for one week at 70° C. It was then cooled to room temperature, and the pH of the extracted water was measured. The result is shown in Table 2.

TABLE 2

| Treated composition | Ex. 1 | Ex. 2 | Ex. 3 | Ex. 4 | Ex. 5 | Comp. Ex. 1 | Comp. Ex. 2 |
|---|---|---|---|---|---|---|---|
| Extracted water pH (prior to heating) | 7.0 | 6.8 | 6.8 | 6.9 | 7.3 | 6.9 | 7.0 |
| Extracted water pH (after heating) | 6.9 | 7.2 | 6.1 | 5.9 | 7.3 | 3.9 | 4.4 |
| Appearance of composition after heating | Paste | Paste | Paste | Paste | Paste | Liquid | Liquid |

The treated composition of this invention had a small pH change even after heating, whereas the pH of the untreated product of Comparative Example 1 dropped considerably, and the composition changed from a paste to a liquid. The treated composition of Comparative Example 2 did lose its odor, but the drop of pH and apparent liquefaction could not be prevented.

Examples 6-12

Using compositions C2-C8, the production amount of propionaldehyde of the target substance treated under identical conditions to those of Example 1, and the pH of the extracted water after heating, were measured. The results are shown in Table 3.

TABLE 3

|  | Ex. 6 | Ex. 7 | Ex. 8 | Ex. 9 | Ex. 10 | Ex. 11 | Ex. 12 |
|---|---|---|---|---|---|---|---|
| Pasty composition C2 | 100.0 | 0 | 0 | 0 | 0 | 0 | 0 |
| Pasty composition C3 | 0 | 100.0 | 0 | 0 | 0 | 0 | 0 |
| Pasty composition C4 | 0 | 0 | 100.0 | 0 | 0 | 0 | 0 |
| Pasty composition C5 | 0 | 0 | 0 | 100.0 | 0 | 0 | 0 |
| Pasty composition C6 | 0 | 0 | 0 | 0 | 100.0 | 0 | 0 |
| Pasty composition C7 | 0 | 0 | 0 | 0 | 0 | 100.0 | 0 |
| Pasty composition C8 | 0 | 0 | 0 | 0 | 0 | 0 | 100.0 |
| 2% succinic acid aqueous solution | 10.0 | 10.0 | 10.0 | 10.0 | 10.0 | 10.0 | 10.0 |
| Propionaldehyde production amount (ppm) | 15.3 | 19.7 | 9.8 | 30.2 | 14.2 | 11.2 | 16.4 |
| Extraction water pH after heating | 6.5 | 6.9 | 6.1 | 6.3 | 5.8 | 7.4 | 7.8 |

Example 13

W/O Type Emulsion

| (Component) | Weight (parts) |
|---|---|
| 1. Treated composition of Example 1 | 10.0 |
| 2. Dimethylpolysiloxane (6 mm$^2$/s (25° C.)) | 12.0 |
| 3. Decamethylcyclopentasiloxane | 10.0 |
| 4. Glyceryl trioctanoate | 5.0 |
| 5. 1,3-butylene glycol | 5.0 |
| 6. Antiseptics | Suitable amount |
| 7. Perfume | Suitable amount |
| 8. Purified water | 58.0 |

(Manufacturing Method)

A: Components 1-5 were mixed uniformly.

B: After mixing components 6-8, they were added to A and emulsified.

The W/O emulsion thus obtained was not tacky, spread lightly, had good skin contact, good setting qualities and sheen.

Example 14

W/O Type Cream

| (Component) | Weight (parts) |
|---|---|
| 1. Treated composition of Example 3 | 6.0 |
| 2. Liquid paraffin | 13.5 |
| 3. Macadamia nut oil | 4.0 |
| 4. Alkyl/polyether comodified silicone (Note 1) | 1.5 |
| 5. Sodium citrate | 0.2 |
| 6. Propylene glycol | 8.0 |
| 7. Glycerol | 3.0 |
| 8. Antiseptic | Suitable amount |
| 9. Perfume | Suitable amount |
| 10. Purified water | 60.8 |

(Note 1)
Shin-Etsu Chemical Co., Ltd.: KF-6026 (commercial name)

(Manufacturing Method)

A: Components 1-4 were mixed.

B: Components 5-10 were mixed, added to A, stirred and emulsified.

The W/O cream thus obtained was not oily or, tacky, spread lightly, had good skin contact, good setting qualities and sheen.

Example 15

W/O Type Cream

| | (Component) | Weight (parts) |
|---|---|---|
| 1. | Treated composition of Example 6 | 7.0 |
| 2. | Liquid paraffin | 13.5 |
| 3. | Macadamia nut oil | 5.0 |
| 4. | Alkyl/polyether co-modified silicone (Note 1) | 0.5 |
| 5. | Hybrid silicone composite powder (Note 2) | 3.0 |
| 6. | Sodium citrate | 0.2 |
| 7. | Propylene glycol | 8.0 |
| 8. | Glycerol | 3.0 |
| 9. | Antiseptics | Suitable amount |
| 10. | Perfume | Suitable amount |
| 11. | Purified water | 59.8 |

(Note 1)
Shin-Etsu Chemical Co., Ltd.: KF-6026 (commercial name)
(Note 2)
Shin-Etsu Chemical Co., Ltd.: KSP-100 (commercial name)

(Manufacturing Method)

A: Components 1-5 were mixed.

B: Components 6-11 were mixed, added to A, stirred and emulsified.

The W/O emulsion thus obtained was not oily or tacky, spread lightly, had good skin contact, good setting qualities and sheen.

Example 16

O/W Type Cream

| | (Component) | Weight (parts) |
|---|---|---|
| 1. | Treated composition of Example 2 | 8.0 |
| 2. | Crosslinking type methyl phenyl polysiloxane (Note 1) | 2.0 |
| 3. | Isotridecyl isononoate | 5.0 |
| 4. | Dipropylene glycol | 7.0 |
| 5. | Glycerol | 5.0 |
| 6. | Methyl cellulose (2% aqueous solution) (Note 2) | 7.0 |
| 7. | Polyacrylamide emulsifier (Note 3) | 2.0 |
| 8. | Guanine | 1.0 |
| 9. | Antiseptic | Suitable amount |
| 10. | Perfume | Suitable amount |
| 11. | Purified water | 63.0 |

(Note 1)
Shin-Etsu Chemical Co., Ltd.: KSG-18
(Note 2)
Shin-Etsu Chemical Co., Ltd.: Metrose SM-4000
(Note 3)
SEPIC: Sepgel 305

(Manufacturing Method)

A: Components 4-11 were mixed.

B: Components 1-3 were mixed and dissolved, A was added, and stirred and emulsified.

The O/W cream thus obtained was fine, spread lightly, was not tacky or oily, was moist and fresh, and left a clean feel.

The cosmetic preparation lasted very well, showed no change with temperature or time, and had excellent stability.

Example 17

W/O Type Cream

| | (Component) | Weight (parts) |
|---|---|---|
| 1. | Treated composition of Example 1 | 7.0 |
| 2. | Dimethylpolysiloxane (6 mm$^2$/s (25° C.)) | 10.0 |
| 3. | Polyether-modified silicone (Note 1) | 0.5 |
| 4. | Dipropylene glycol | 10.0 |
| 5. | Sodium citrate | 0.2 |
| 6. | Ethanol | 5.0 |
| 7. | Antiseptic | Suitable amount |
| 8. | Perfume | Suitable amount |
| 9. | Purified water | 67.8 |

(Note 1)
Shin-Etsu Chemical Co., Ltd.: KF-6017 (commercial name)

(Manufacturing Method)

A: Components 1-3 were heated and dissolved.

B: Components 4-9 were mixed and dissolved, added to A, stirred and emulsified.

The W/O cream thus obtained was moist and fresh, not oily or tacky, spread lightly, and had a fresh, clean feel. It had good skin contact and setting qualities, and gave a matt finish.

Example 18

W/O Type Makeup Foundation

| (Component) | Weight (parts) |
|---|---|
| 1. Treated composition of Example 4 | 5.0 |
| 2. Crosslinking type dimethylpolysiloxane (Note 1) | 1.0 |
| 3. Polyether-modified silicone (Note 2) | 0.5 |
| 4. Dimethylpolysiloxane (6 mm$^2$/s (25° C.)) | 6.0 |
| 5. Dimethylpolysiloxane (20 mm$^2$/s (25° C.)) | 2.0 |
| 6. Decamethylcyclopentasiloxane | 3.0 |
| 7. Titanium oxide/cyclopentasiloxane dispersion (Note 3) | 10.0 |
| 8. Dipropylene glycol | 5.0 |
| 9. Sodium citrate | 0.2 |
| 10. Methyl cellulose (2% aqueous solution) (Note 4) | 2.5 |
| 11. Ethanol | 3.0 |
| 12. Antiseptic | Suitable amount |
| 13. Perfume | Suitable amount |
| 14. Purified water | 62.8 |

(Note 1)
Shin-Etsu Chemical Co., Ltd.: KSG-15 (commercial name)
(Note 2)
Shin-Etsu Chemical Co., Ltd.: KF-6017 (commercial name)
(Note 3)
Shin-Etsu Chemical Co., Ltd. SPD-T1S (commercial name)
(Note 4)
Shin-Etsu Chemical Co., Ltd. Metrose 65-SH4000 (commercial name)

(Manufacturing Method)

A: Components 1-7 were mixed.

B: Components 8-14 were mixed and dissolved, added to A, stirred and emulsified.

The W/O makeup foundation thus obtained was not oily or tacky, spread lightly, and had a fresh, clean feel. It had good skin contact and setting qualities, and gave a matt finish. Moreover, it had an ultraviolet cut action and lasted well in cosmetics.

Example 19

O/W Type Cream

| (Component) | Weight (parts) |
|---|---|
| 1. Treated composition of Example 1 | 2.0 |
| 2. Crosslinking type dimethylpolysiloxane (Note 1) | 15.0 |
| 3. Decamethyl cyclopentasiloxane | 10.0 |
| 4. Dimethylpolysiloxane (6 mm$^2$/s (25° C.)) | 18.0 |
| 5. Polyether-modified silicone (Note 2) | 0.7 |
| 6. Propylene glycol | 3.0 |
| 7. Polyacrylamide mixture (Note 3) | 0.8 |
| 8. Xanthan gum (2% aqueous solution) | 8.0 |
| 9. Antiseptic | Suitable amount |
| 10. Perfume | Suitable amount |
| 11. Purified water | 42.5 |

(Note 1)
Shin-Etsu Chemical Co., Ltd.: KSG-16 (commercial name)
(Note 2)
Shin-Etsu Chemical Co., Ltd.: KF-6011 (commercial name)
(Note 3)
SEPIC Sepgel 305 (commercial name)

(Manufacturing Method)

A: Components 1-4 were heated and mixed.

B: Components 5-11 were mixed and dissolved.

C: A was added to B, stirred and emulsified.

The O/W cream thus obtained was fine, spread lightly, was not tacky or oily, was moist and fresh, and left a clean feel. The cosmetic preparation lasted very well, showed no change with temperature or time, and had excellent stability.

Example 20

Lipstick

| (Component) | Weight (parts) |
|---|---|
| 1. Polyethylene wax | 12.0 |
| 2. Microcrystalline wax | 4.0 |
| 3. Polybutene | 5.0 |
| 4. Acrylate/dimethyl silicone copolymer (Note 1) | 12.0 |
| 5. Treatment composition of Example 7 | 7.0 |
| 6. Cetyl octanoate | 20.0 |
| 7. Cane sugar fatty acid ester | 3.0 |
| 8. Glyceryl isostearate | 37.0 |
| 9. Pigment | Suitable amount |
| 10. Antiseptics | Suitable amount |
| 11. Perfume | Suitable amount |

(Note 1)
Shin-Etsu Chemical Co., Ltd.: KP-561

(Manufacturing Method)

A: Components 1-7 and part of Component 8 were heated, mixed and dissolved.

B: Components 9-11 and the remainder of Component 8 were uniformly mixed, added to A, and homogenized.

The lipstick thus obtained spread lightly, was not oily or powdery, and left a clean feel. It had good water resistance and water repellence, lasted well, and had excellent stability.

Example 21

Powder Foundation

| (Component) | Weight (parts) |
|---|---|
| 1. Vaseline | 2.5 |
| 2. Squalane | 3.0 |
| 3. Treatment composition of Example 5 | 0.5 |
| 4. Glyceryl trioctanoate | 2.0 |
| 5. Silicone-treated mica | 40.0 |
| 6. Silicone-treated talc | Remainder |
| 7. Silicone-treated titanium oxide | 10.0 |
| 8. Silicone-treated particulate titanium oxide | 5.0 |
| 9. Silicone-treated barium sulfate | 10.0 |
| 10. Pigment | Suitable amount |
| 11. Fluorine-modified hybrid silicone composition powder (Note 1) | 2.0 |
| 12. Silicone powder (Note 2) | 2.5 |
| 13. Antiseptics | Suitable amount |
| 14. Perfume | Suitable amount |

(Note 1)
Shin-Etsu Chemical Co., Ltd.: KSP-200 (commercial name)
(Note 2)
Shin-Etsu Chemical Co., Ltd.: KMP-590 (commercial name)

(Manufacturing Method)

A: Components 4-13 were mixed, and homogenized.

B: Components 1-3 were mixed uniformly, added to A, and homogenized.

C: Component 14 was added to B, and press molded into a mold to obtain a foundation.

The powder foundation thus obtained was not tacky, spread lightly, had good skin contact, good setting qualities and sheen.

Example 22

Cream Foundation

| (Component) | Weight (parts) |
|---|---|
| 1. Treatment composition of Example 7 | 5.5 |
| 2. Glyceryl trioctanoate | 4.0 |
| 3. Dimethylpolysiloxane (6 mm$^2$/s (25° C.)) | 5.0 |
| 4. Decamethyl cyclopentasiloxane | 6.0 |
| 5. Fluorine-modified hybrid silicone composition powder (Note 1) | 2.5 |
| 6. Pigment | 8.0 |
| 7. Acrylic silicone resin (Note 2) | 5.0 |
| 8. Dipropylene glycol | 5.0 |
| 9. Sodium citrate | 0.2 |
| 10. Antiseptics | Suitable amount |
| 11. Perfume | Suitable amount |
| 12. Purified water | 59.3 |

(Note 1)
Shin-Etsu Chemical Co., Ltd. KSP-200 (commercial name)
(Note 2)
Shin-Etsu Chemical Co., Ltd. KP-545 (commercial name)

(Manufacturing Method)

A: Components 1-5 were heated and mixed.

B: Components 8-12 were mixed and dissolved, added to A, stirred and emulsified.

C: Components 6-7 were mixed, added to B, and homogenized.

The cream foundation thus obtained was not tacky, spread lightly, had good skin contact, good setting qualities, and gave a matt finish.

Example 23

W/O Compact Foundation

| (Component) | Weight (parts) |
|---|---|
| 1. Ceresin | 5.5 |
| 2. Microcrystalline wax | 1.0 |
| 3. Liquid paraffin | 3.0 |
| 4. Treatment composition of Example 3 | 9.0 |
| 5. Dicapric acid polypropylene glycol | 3.0 |
| 6. Alkyl/polyether co-modified organopolysiloxane (Note) | 1.0 |
| 7. Dimethylpolysiloxane (6 $mm^2$/s (25° C.)) | 15.5 |
| 8. Oil-treated titanium oxide | 10.0 |
| 9. Pigment | Suitable amount |
| 10. Lecithin | 0.3 |
| 11. Monooleic acid polyoxyethylene sorbitan | 0.5 |
| 12. Dipropylene glycol | 8.0 |
| 13. Sodium citrate | 0.2 |
| 14. Purified water | Remainder |

(Note 1)
Shin-Etsu Chemical Co., Ltd. KF-6026 (commercial name)

(Manufacturing Method)

A: Components 1-7 were heated and mixed.

B: Components 8-12 were mixed uniformly.

C: Components 13-14 were mixed, B was added, mixed uniformly and heated.

D: C was added to A and emulsified.

It was found that although this W/O compact foundation contained a large amount of oil, it was not oily or tacky, spread lightly, had a clean feel, good skin contact and good setting qualities.

Example 24

Eye Shadow

| (Component) | Weight (parts) |
|---|---|
| 1. Sericite | 40.0 |
| 2. Mica | 10.0 |
| 3. Talc | Remainder |
| 4. Titanium oxide | 10.0 |
| 5. Particulate titanium oxide | 5.0 |
| 6. Magnesium stearate | 3.0 |
| 7. Pigment | Suitable amount |
| 8. Octyl dodecanol | 3.0 |
| 9. Dimethylpolysiloxane (6 $mm^2$/s (25° C.)) | 4.0 |
| 10. Treatment composition of Example 2 | 6.0 |
| 11. Antiseptics | Suitable amount |
| 12. Perfume | Suitable amount |

(Manufacturing Method)

A: Components 8-11 were heated and mixed.

B: Components 1-7 were mixed, A was added and mixed uniformly.

C: Component 12 was added to B.

The eye shadow thus obtained was not tacky, spread lightly, had good skin contact, good setting qualities and sheen, and lasted well in cosmetics.

Example 25

Powder Eyebrow

| (Component) | Weight (parts) |
|---|---|
| 1. Vaseline | 2.5 |
| 2. Dimethylpolysiloxane (6 $mm^2$/s (25° C.)) | 1.5 |
| 3. Treatment composition of Example 4 | 0.5 |
| 4. Glyceryl trioctanoate | 4.0 |
| 5. Silicone-treated mica | 40.0 |
| 6. Silicone-treated talc | Remainder |
| 7. Silicone-treated titanium oxide | 10.0 |
| 8. Silicone-treated barium sulfate | 15.0 |
| 9. Silicone-treated pigment | Suitable amount |
| 10. Hybrid Silicone composite powder (Note 1) | 1.5 |
| 11. Spherical polymethylsilsesquioxane fine particles (Note 2) | 2.5 |
| 12. Antiseptic | Suitable amount |
| 13. Perfume | Suitable amount |

(Note 1)
Shin-Etsu Chemical Co., Ltd.: KSP-100 (commercial name)
(Note 2)
Shin-Etsu Chemical Co., Ltd. KMP-590 (commercial name)

(Manufacturing Method)

A: Components 5-12 were mixed and homogenized.

B: Components 1-4 were mixed uniformly, added to A, and the mixture homogenized.

C: Component 13 was added to B, and the mixture pressed in a mold to obtain a powder eyebrow.

The eyebrow thus obtained was not tacky, spread lightly, had good skin contact, good setting qualities and sheen, and lasted well in cosmetics.

Example 26

Hair Cream

| (Component) | Weight (parts) |
|---|---|
| 1. Treatment composition of Example 1 | 2.0 |
| 2. Dimethylpolysiloxane (6 $mm^2$/s (25° C.)) | 5.0 |
| 3. Decamethyl cyclopentasiloxane | 8.0 |
| 4. Stearyl trimethylammonium chloride | 1.5 |
| 5. Glycerol | 3.0 |
| 6. Propylene glycol | 5.0 |
| 7. Hydroxyethylcellulose | 0.2 |
| 8. Antiseptic | Suitable amount |
| 9. Perfume | Suitable amount |
| 10. Purified water | 75.3 |

(Manufacturing Method)

A: Components 1-3 were heated and dissolved.

B: Components 4-8 and 10 were uniformly mixed and dissolved.

C: B was added to A, emulsified, cooled, and Component 9 was added.

The hair cream thus obtained spread easily, and left the hair very soft, smooth, manageable, moist and glossy.

Example 27

Conditioning Mousse

| (Component) | Weight (parts) |
|---|---|
| 1. Treatment composition of Example 6 | 0.5 |
| 2. Dimethylpolysiloxane (6 mm$^2$/s (25° C.)) | 2.0 |
| 3. Crosslinking type dimethylpolysiloxane (Note 1) | 0.5 |
| 4. Glyceryl trioctanoate | 1.5 |
| 5. Glycerol | 3.0 |
| 6. Stearyldimethyl benzylammonium chloride | 0.5 |
| 7. Polyoxyethylene-hardened castor oil | 0.5 |
| 8. Ethanol | 7.0 |
| 9. Antiseptic | Suitable amount |
| 10. Perfume | Suitable amount |
| 11. Purified water | Remainder |
| 12. Liquefied petroleum gas | 5.0 |

(Note 1)
Shin-Etsu Chemical Co., Ltd. KSG-16 (commercial name)

(Manufacturing Method)

A: Components 1-4 were heated and dissolved.

B: Components 5-9 and 11 were mixed uniformly and dissolved.

C: B was added to A, emulsified, cooled, and Component 10 was added.

D: An aerosol can was filled with C, and a conditioning mousse was obtained. The conditioning mousse thus obtained was moist, flexible, very smooth, not oily and left a good feeling. It also had good skin contact and setting qualities, and gave a matt finish.

Example 28

Roll-on Type Antiperspirant

| (Component) | Weight (parts) |
|---|---|
| 1. Treatment composition of Example 1 | 25.0 |
| 2. Dimethylpolysiloxane (6 mm$^2$/s (25° C.)) | 10.0 |
| 3. Crosslinking type dimethylpolysiloxane (Note 1) | 15.0 |
| 4. Decamethyl cyclopentasiloxane | 30.0 |
| 5. Aluminium zirconium tetrachlorohydrate | 20.0 |
| 6. Perfume | Suitable amount |

(Note 1)
Shin-Etsu Chemical Co., Ltd. KSG-15 (commercial name)

(Manufacturing Method)

A: Components 1-4 were heated and mixed.

B: Components 5 and 6 were added to A, and dispersed uniformly.

The roll-on antiperspirant thus obtained spread lightly, was cool and fresh, not tacky or oily, showed no change with temperature or time, was easy to use, and very stable.

Example 29

W/O Type Antiperspirant

| (Component) | Weight (parts) |
|---|---|
| 1. Treatment composition of Example 2 | 9.0 |
| 2. Decamethyl cyclopentasiloxane | 7.0 |
| 3. Glyceryl trioctanoate | 8.0 |
| 4. 1,3-butylene glycol | 5.0 |
| 5. Sodium citrate | 0.2 |
| 6. Aluminium chlorohydrate | 20.0 |
| 7. Perfume | Suitable amount |
| 8. Purified water | 50.8 |

(Manufacturing Method)

A: Components 1-3 were heated and mixed.

B: Components 4-5 and 8 were mixed, and Components 6 and 7 were added and dissolved. C: B was added to A, stirred and emulsified.

The W/O antiperspirant thus obtained spread lightly, was cool and fresh, not tacky or oily, showed no change with temperature or time, was easy to use, and very stable.

Example 30

W/O Type UV Cut Cream

| (Component) | Weight (parts) |
|---|---|
| 1. Silicone-treated zinc oxide | 20.0 |
| 2. Acrylate/dimethylpolysiloxane copolymer (Note 1) | 12.0 |
| 3. Decamethyl cyclopentasiloxane | 20.0 |
| 4. Glyceryl trioctanoate | 3.0 |
| 5. Treatment composition of Example 8 | 7.0 |
| 6. Polyether-modified silicone (Note 2) | 1.0 |
| 7. Alkyl/polyether co-modified silicone (Note 3) | 1.0 |
| 8. Octyl methoxycinnamate | 6.0 |
| 9. Sodium citrate | 0.2 |
| 10. Dipropylene glycol | 3.0 |
| 11. Antiseptic | Suitable amount |
| 12. Perfume | Suitable amount |
| 13. Purified water | 26.8 |

(Note 1)
Shin-Etsu Chemical Co., Ltd.: KP-545 (commercial name)
(Note 2)
Shin-Etsu Chemical Co., Ltd.: KF-6017 (commercial name)
(Note 3)
Shin-Etsu Chemical Co., Ltd.: KF-6026 (commercial name)

(Manufacturing Method)

A: Part of Component 3 and Components 4-8 were heated and mixed.

B: Components 9-11 and 13 were mixed, added to A, stirred and emulsified.

C: Components 1, 2 and the remainder of Component 3 were mixed and dispersed, Component 12 was added to B, and the mixture homogenized.

The W/O UV cut cream thus obtained spread lightly, was fresh, not tacky or oily, was transparent, lasted well in cosmetics, showed no change with temperature or time, was easy to use, and very stable.

Example 31

W/O Type UV Cut Milky Lotion

| (Component) | Weight (parts) |
|---|---|
| 1. Dimethylpolysiloxane (6 mm$^2$/s (25° C.)) | 5.0 |
| 2. Glyceryl trioctanoate | 2.0 |
| 3. Treatment composition of Example 1 | 6.0 |
| 4. Polyether-modified silicone (Note 1) | 1.0 |
| 5. Titanium oxide/decamethyl cyclopentasiloxane dispersion (Note 2) | 30.0 |
| 6. Zinc oxide/decamethyl cyclopentasiloxane dispersion (Note 3) | 30.0 |
| 7. Dipropylene glycol | 3.0 |
| 8. Sodium citrate | 0.2 |
| 9. Antiseptic | Suitable amount |
| 10. Perfume | Suitable amount |
| 11. Purified water | 22.8 |

(Note 1)
Shin-Etsu Chemical Co., Ltd.: KF-6017 (commercial name)
(Note 2)
Shin-Etsu Chemical Co., Ltd. SPD-T1S (commercial name)
(Note 3)
Shin-Etsu Chemical Co., Ltd.: SPD-Z1 (commercial name)

(Manufacturing Method)

A: Components 1-4 were heated and mixed.

B: Components 7-9 and Component 11 were mixed and dissolved, added to A, stirred and emulsified.

C: Components 5, 6 and 10 were added to B, and homogenized.

The UV cut milky lotion thus obtained was a W/O UV cut milky lotion which spread lightly, was fresh, not tacky or oily, was transparent, lasted well in cosmetics, showed no change with temperature or time, was easy to use, and very stable.

Example 32

O/W Type UV Cut Cream

| (Component) | Weight (parts) |
|---|---|
| 1. Crosslinking type organopolysiloxane (Note 1) | 5.0 |
| 2. Cetyl isooctanoate | 5.0 |
| 3. Treatment composition of Example 4 | 1.0 |
| 4. Titanium oxide/decamethyl cyclopentasiloxane dispersion (Note 2) | 15.0 |
| 5. Polyether-modified silicone (Note 3) | 1.0 |
| 6. Polyether-modified silicone (Note 4) | 1.0 |
| 7. Acrylic acid amide mixture (Note 5) | 2.0 |
| 8. Propylene glycol | 5.0 |
| 9. Methylcellulose (2% aqueous solution) (Note 6) | 5.0 |
| 10. Antiseptic | Suitable amount |
| 11. Perfume | Suitable amount |
| 12. Purified water | 60.0 |

(Note 1)
Shin-Etsu Chemical Co., Ltd.: KSG-18 (commercial name)
(Note 2)
Shin-Etsu Chemical Co., Ltd.: SPD-T1S (commercial name)
(Note 3)
Shin-Etsu Chemical Co., Ltd.: KF-6027 (commercial name)
(Note 4)
Shin-Etsu Chemical Co., Ltd.: KF-6011 (commercial name)
(Note 5)
Seppie: Sepigel 305 (commercial name)
(Note 6)
Shin-Etsu Chemical Co., Ltd.: Metrose SM-4000 (commercial name)

(Manufacturing Method)

A: Components 5-8, 10 and 12 were mixed.

B: Components 1-3 were heated and mixed, added to A, stirred and emulsified.

C: Component 4 was added to B, Components 9 and 11 were added, and homogenized.

The UV cut cream thus obtained was a W/O UV cut cream which spread lightly, was fresh, not tacky or oily, transparent, lasted well in cosmetics, showed no change with temperature or time, was easy to use, and very stable.

Example 33

Nonaqueous Emulsion

| (Component) | Weight (parts) |
|---|---|
| 1. Crosslinking type silicone resin/decamethyl cyclopentasiloxane (Note 1) | 30.0 |
| 2. Decamethyl cyclopentasiloxane | 15.0 |
| 3. Dimethylpolysiloxane (6 mm$^2$/s) | 7.0 |
| 4. Treatment composition of Example 1 | 3.0 |
| 5. Dimethyl distearyl ammonium hectorite | 2.0 |
| 6. Sodium chloride | 0.1 |
| 7. 1,3-butylene glycol | 40.9 |

(Note 1)
Crosslinking type silicone resin/decamethyl cyclopentasiloxane: KSG15 (Shin-Etsu Chemical Co., Ltd.)

(Manufacturing Method)

A: Components 1-5 were mixed uniformly.

B: Components 6 and 7 were mixed.

C: B was added to A and emulsified uniformly.

The nonaqueous emulsion thus obtained spread lightly, was not tacky or oily, left the skin feeling soft, and was very stable.

Example 34

W/O/W Type Cream

| (Component) | Weight (parts) |
|---|---|
| 1. Cetyl isooctanoate | 5.0 |
| 2. Treatment composition of Example 5 | 6.0 |
| 3. Decamethyl cyclopentasiloxane | 5.0 |
| 4. Dioleic acid methyl glucose | 1.5 |
| 5. Isohexadecane | 3.5 |
| 6. Magnesium sulfate | 0.5 |
| 7. Propylene glycol | 5.0 |
| 8. Purified water | 39.5 |
| 9. Cetyl alcohol | 1.0 |
| 10. PEG-10 soya sterol | 2.0 |
| 11. Antiseptic | Suitable amount |
| 12. Perfume | Suitable amount |
| 13. Purified water | 31.0 |

(Manufacturing Method)

A: Components 6-8 were mixed.

B: Components 1-5 were mixed, added to A, stirred and emulsified.

C: Components 9-11 and 13 were mixed, B was added with stirring, and emulsified.

D: Component 12 was added to C, and homogenized.

The W/O/W cream thus obtained spread lightly, left a clean feeling, was not tacky or oily, was transparent, lasted well in cosmetics, showed no change with temperature or time, was easy to use and very stable.

Example 35

O/W/O Type Milky Lotion

| (Component) | Weight (parts) |
|---|---|
| 1. Glyceryl trioctanoate | 15.0 |
| 2. Treatment composition of Example 7 | 8.0 |
| 3. Cane sugar monostearate | 3.0 |
| 4. Glycerol | 5.0 |
| 5. 1,3-butylene glycol | 5.0 |
| 6. Antiseptic | Suitable amount |
| 7. Purified water | 60.0 |
| 8. Macadamia nut oil | 2.0 |
| 9. Cetyl alcohol | 2.0 |
| 10. Perfume | Suitable amount |

(Manufacturing Method)
A: Components 1-2 were mixed uniformly.
B: Components 3-7 were heated and mixed, and homogenized.
C: Components 8-10 were heated and mixed.
D: B was stirred, C was added and emulsified, and cooled.
E: A was stirred, and D was added and emulsified.

The O/W/O cream thus obtained spread lightly, left a clean feeling, was not tacky or oily, was transparent, lasted well in cosmetics, showed no change with temperature or time, was easy to use and very stable.

Example 36

O/W/O Type Facial Liquid Foundation

| (Component) | Weight (parts) |
|---|---|
| 1. Treatment composition of Example 5 | 7.0 |
| 2. Decanoic acid propylene glycol | 5.0 |
| 3. Isopropyl myristate | 5.0 |
| 4. Pigment | 10.0 |
| 5. Egg yolk-derived hydrogenated phospholipid | 1.0 |
| 6. Glycerol | 2.0 |
| 7. 1,3-butylene glycol | 10.0 |
| 8. Antiseptic | Suitable amount |
| 9. Purified water | 52.0 |
| 10. Squalane | 3.0 |
| 11. Cetyl alcohol | 5.0 |
| 12. Perfume | Suitable amount |

(Manufacturing Method)
A: Components 1-3 were mixed uniformly.
B: Components 4-9 were heated and mixed.
C: Components 10-12 were heated and mixed.
D: B was stirred, C was added, emulsified, and cooled.
D: A was stirred, D was added, and emulsified,.

The O/W/O liquid foundation thus obtained spread lightly, left a clean feeling, was not tacky or oily, was transparent, lasted well in cosmetics, showed no change with temperature or time, was easy to use and very stable.

Industrial Field of Application

The cosmetic material formed by blending the hydrophilic organic group-containing crosslinking type organopolysiloxane polymer purified according to this invention and an oil, is not tacky or heavy when it is applied, feels soft, spreads lightly, and leaves the skin feeling clean and smooth. When it is applied, it imparts flexibility, smoothness and an emollient effect without losing moisture by evaporation. It imparts a natural sheen or matte finish, is very easy to use, and has good stability over time. Moreover, according to this invention, a cosmetic material which has good storage stability and can prevent unpleasant odors can be provided, therefore this invention has considerably wide industrial application.

What is claimed is:

1. A pasty composition obtained by adding at least one acidic substance selected from citric acid, lactic acid, malic acid, glutamic acid, tartaric acid, acetic acid, glycine, succinic acid, sodium dihydrogen phosphate, and mixtures thereof, to a mixture comprising a crosslinking organopolysiloxane polymer having a polyoxyalkylene group and a liquid oil, heating the resultant mixture of said at least one acidic substance, said crosslinking organopolysiloxane polymer having a polyoxyalkylene group, and said liquid oil to 50-100° C., thereafter adding a basic neutralizing agent to adjust the pH to 5-8, and thereafter removing volatile components by heating to 20-150° C. and/or decompression, wherein the proportions of said acidic substance and basic neutralizer are respectively 0.01-10 wt parts relative to 100 wt parts of said crosslinking organopolysiloxane polymer;

wherein when an identical amount of water is added to said composition and the resultant mixture is heated at 60° C. for 24 hours the amount of propionaldehyde produced is 100 ppm or less;

wherein said polymer is insoluble in organic solvents, and can swell by containing at least its own weight of decamethyl cyclopentasiloxane, and said crosslinking organopolysiloxane polymer is formed by an addition polymerization of at least one organohydrogen polysiloxane selected from those represented by formula (A1) and formula (A2), and at least one unsaturated compound selected from those represented by formulas (B1), (B2) and (B3):

$R^1_a R^2_b H_c SiO_{(4-a-b-c)/2}$ (A1)

$R^1_d H_e SiO_{(4-d-e)/2}$ (A2)

$C_f H_{2f-1} O(C_g H_{2g} O)_h C_f H_{2f-1}$ (B1)

(B2)

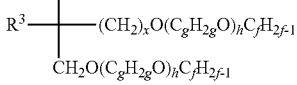

(B3)

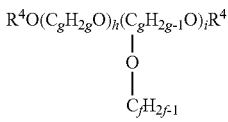

wherein, in these formulae, $R^1$ in each case is a monofunctional hydrocarbon group having 1-30 carbon atoms and does not contain an alkenyl group, and which is unsubstituted or optionally substituted, said $R^1$ groups may be identical or different;

$R^2$ in each case is an organic group of the formula $-C_f H_{2f} O(C_g H_{2g} O)_h R^6$, said $R^2$ groups may identical or different;

R³ is a hydrogen atom, or a monofunctional hydrocarbon group having 1-10 carbon atoms which is unsubstituted or optionally substituted, and which does not contain an alkenyl group;

R⁴ in each case is an organic group which is identical to R³ or is of the formula —$C_fH_{2f-1}$, said R⁴ groups may identical or different;

R⁶ is a hydrogen atom, or a monofunctional hydrocarbon group not containing an aliphatic unsaturated group which is unsubstituted or optionally substituted, or an acetyl group;

a, b, c, d, and e are $1.0 \le a \le 2.3$, $0.001 \le b \le 1.0$, $0.001 \le c \le 1.0$, $1.0 \le d \le 2.3$, and $0.001 \le e \le 1.0$, respectively, and are positive numbers satisfying the relations $1.5 \le a+b+c \le 2.6$ and $1.5 \le d+e \le 2.6$, f is an integer from 2-6, g is an integer from 2-4, h is an integer from 1-200, i is an integer from 2-10, and x is 0 or 1.

2. The pasty composition according to claim 1, wherein when an identical amount of water is added to the composition and heated to 70° C. for one hour, the pH of water extracted from the composition is 6.0 or more.

3. The pasty composition according to claim 1, wherein said basic neutralizing agent is selected from among sodium carbonate, sodium hydrogen carbonate, sodium hydroxide, potassium hydroxide, disodium hydrogen phosphate, sodium acetate and mixtures thereof.

4. The pasty composition according to claim 1, wherein said crosslinking organopolysiloxane polymer is a polymer comprising the organohydrogen polysiloxane (A2) and polyoxyalkylene (B1).

5. The pasty composition according to claim 1, wherein said liquid oil is selected from among silicone oil, hydrocarbon oil, ester oil, natural animal/vegetable oil, semi-synthetic oil, and mixtures thereof.

6. A cosmetic material formed by blending the pasty composition according to claim 1.

7. The cosmetic according to claim 6, further comprising water as Component C).

8. The cosmetic according to claim 6, further comprising a compound having an alcoholic hydroxyl group in the molecular structure as Component D).

9. The cosmetic according to claim 6, further comprising a water-soluble or water-swelling polymer as Component E).

10. The cosmetic according to claim 6, further comprising a powder and/or colorant as Component F).

11. The cosmetic according to claim 10, wherein at least part of said powder and/or colorant is a crosslinking spherical silicone fine powder having a structure wherein dimethylpolysiloxane is crosslinked, a cros slinking spherical polymethylsilsesquioxane fine powder, or a fine powder formed by coating a crosslinked spherical silicone rubber surface with polymethylsilsesquioxane particles.

12. The cosmetic according to claim 6, further comprising a surfactant as Component G).

13. The cosmetic according to claim 12, wherein said surfactant G) is a straight-chain or branched organopolysiloxane having a polyoxyalkylene chain in the molecule.

14. The cosmetic according to claim 12, wherein the HLB of said surfactant G) is 2-8.

15. The cosmetic according to claim 6, further comprising a composition comprising a crosslinking organopolysiloxane polymer without hydrophilicity and a liquid oil as Component H).

16. The cosmetic according to claim 6, further comprising a silicone resin as Component I).

17. The cosmetic according to claim 16, wherein said silicone resin I) is an acrylic silicone resin.

18. The cosmetic according to claim 16, wherein said silicone resin I) is an acrylic silicone resin containing at least one anionic organic group selected from among a pyrrolidone group, long-chain alkyl group, polyoxyalkylene group, fluoroalkyl group and carboxyl group.

19. The cosmetic according to claim 16, wherein said Component I) is at least one silicone resin selected from resins comprising a $R^1_3SiO_{0.5}$ unit and $SiO_2$ unit, resins comprising a $R^1_3SiO_{0.5}$ unit, $R^1_2SiO$ unit and $SiO_2$ unit, resins comprising a $R^1_3SiO_{0.5}$ unit and $R^1SiO_{1.5}$ unit, resins comprising a $R^1_3SiO_{0.5}$unit, $R^1_2SiO$ unit and $R^1SiO_{1.5}$ unit, and resins comprising a $R^1_3SiO_{0.5}$ unit, $R^1_2SiO$ unit, $R^1SiO_{1.5}$ unit and $SiO_2$ unit.

20. The cosmetic according to claim 16, wherein said Component I) is a silicone resin containing at least one anionic organic group selected from a pyrrolidone group, long-chain alkyl group, polyoxyalkylene group, fluoroalkyl group and carboxyl group.

21. A skin care cosmetic containing the cosmetic material according to claim 6.

22. A makeup cosmetic containing the cosmetic material according to claim 6.

23. A hair care cosmetic containing the cosmetic material according to claim 6.

24. An antiperspirant cosmetic containing the cosmetic material according to claim 6.

25. An ultraviolet cut cosmetic containing the cosmetic material according to claim 6.

26. The cosmetic material according to claim 6, which is in the form of a liquid, emulsion, cream, solid, paste, gel, powder, laminate, mousse, spray or stick.

27. A method for manufacturing a pasty composition comprising:

adding at least one acidic substance selected from citric acid, lactic acid, malic acid, glutamic acid, tartaric acid, acetic acid, glycine, succinic acid, sodium dihydrogen phosphate, and mixtures thereof, to a mixture comprising a crosslinking organopolysiloxane polymer having a polyoxyalkylene group and a liquid oil, and heating the resultant mixture of said at least one acidic substance, said crosslinking organopolysiloxane polymer having a polyoxyalkylene group, and said liquid oil to 50-100° C., then adding a basic neutralizing agent to adjust the pH to 5-8, and then removing volatile components by heating to 20-150° C. and/or decompression, wherein the proportions of said acidic substance and basic neutralizer are respectively 0.01-10 wt parts relative to 100 wt parts of said crosslinking organopolysiloxane polymer;

wherein when an identical amount of water is added to said composition and the resultant mixture is heated at 60° C. for 24 hours the amount of propionaldehyde produced is 100 ppm or less;

wherein said polymer is insoluble in organic solvents, and can swell by containing at least its own weight of decamethyl cyclopentasiloxane, and said crosslinking organopolysiloxane polymer is formed by an addition polymerization of at least one organohydrogen polysiloxane selected from those represented by formula (A1) and formula (A2), and at least one unsaturated compound selected from those represented by formulas (B1), (B2) and (B3):

$$R^1_a R^2_b H_c SiO_{(4-a-b-c)/2} \quad (A1)$$

$$R^1_d H_e SiO_{(4-d-e)/2} \quad (A2)$$

$$C_f H_{2f-1} O(C_g H_{2g} O)_h C_f H_{2f-1} \quad (B1)$$

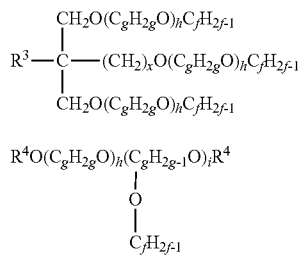

$$R^4 O(C_g H_{2g} O)_h (C_g H_{2g-1} O)_i R^4$$
$$|$$
$$O$$
$$|$$
$$C_f H_{2f-1}$$
(B3)

wherein, in these formulae, $R^1$ in each case is a monofunctional hydrocarbon group having 1-30 carbon atoms and does not contain an alkenyl group, and which is unsubstituted or optionally substituted, said $R^1$ groups may be identical or different;

$R^2$ in each case is an organic group of the formula —$C_f H_{2f} O(C_g H_{2g} O)_h R^6$, said $R^2$ groups may identical or different;

$R^3$ is a hydrogen atom, or a monofunctional hydrocarbon group having 1-10 carbon atoms which is unsubstituted or optionally substituted, and which does not contain an alkenyl group;

$R^4$ in each case is an organic group which is identical to $R^3$ or is of the formula —$C_f H_{2f-1}$, said $R^4$ groups may identical or different;

$R^6$ is a hydrogen atom, or a monofunctional hydrocarbon group not containing an aliphatic unsaturated group which is unsubstituted or optionally substituted, or an acetyl group;

a, b, c, d, and e are $1.0 \leq a \leq 2.3$, $0.001 \leq b \leq 1.0$, $0.001 \leq c \leq 1.0$, $1.0 \leq d \leq 2.3$, and $0.001 \leq e \leq 1.0$, respectively, and are positive numbers satisfying the relations $1.5 \leq a+b+c \leq 2.6$ and $1.5 \leq d+e \leq 2.6$, f is an integer from 2-6,
g is an integer from 2-4,
h is an integer from 1-200,
i is an integer from 2-10, and
x is 0 or 1.

28. The method of manufacturing the pasty composition according to claim 27, wherein said acidic substance and said basic neutralizing agent produce a salt that has a buffer effect.

29. The method of manufacturing the pasty composition according to claim 27, wherein said basic neutralizing agent is selected from sodium carbonate, sodium hydrogen carbonate, sodium hydroxide, potassium hydroxide, disodium hydrogen phosphate, sodium acetate and mixtures thereof.

30. The pasty composition according to claim 5, wherein said liquid oil is a silicone oil.

31. The pasty composition according to claim 1, wherein said basic neutralizing agent is selected from among sodium carbonate, sodium hydrogen carbonate, sodium hydroxide, potassium hydroxide, disodium hydrogen phosphate, sodium acetate and mixtures thereof; and said liquid oil is a silicone oil.

\* \* \* \* \*